United States Patent
Sato et al.

(10) Patent No.: US 6,790,380 B2
(45) Date of Patent: Sep. 14, 2004

(54) STERILIZING COMPOSITION AND METHOD FOR STERILIZING USING THE SAME

(75) Inventors: Jun Sato, Saitama (JP); Katsuko Hiraguri, Fukushima (JP)

(73) Assignee: Nippon Peroxide Co., Ltd., Kawasaki (JP)

( * ) Notice: Subject to any disclaimer, the term of this patent is extended or adjusted under 35 U.S.C. 154(b) by 0 days.

(21) Appl. No.: 10/327,112

(22) Filed: Dec. 24, 2002

(65) Prior Publication Data

US 2003/0234382 A1 Dec. 25, 2003

(30) Foreign Application Priority Data

Jun. 21, 2002 (JP) ........................................ 2002-181323

(51) Int. Cl.⁷ ............................................. A01N 59/00
(52) U.S. Cl. .................................. 252/186.23; 424/616
(58) Field of Search ....................... 252/186.23; 424/616

(56) References Cited

U.S. PATENT DOCUMENTS

| | | | |
|---|---|---|---|
| 4,051,058 A | * 9/1977 | Bowing et al. | ............. 424/616 |
| 4,900,721 A | * 2/1990 | Bansemir et al. | ............. 514/25 |
| 4,917,815 A | * 4/1990 | Beilfuss et al. | ........ 252/186.23 |
| 5,368,867 A | * 11/1994 | Da Silva et al. | ............. 424/616 |
| 5,451,346 A | * 9/1995 | Amou et al. | ........... 252/186.23 |
| 5,900,256 A | * 5/1999 | Scoville et al. | ............. 424/616 |
| 6,514,509 B2 | * 2/2003 | Tabasso | ..................... 424/405 |
| 6,635,286 B2 | * 10/2003 | Hei et al. | ................... 424/616 |
| 2002/0168422 A1 | 11/2002 | Hei et al. | |
| 2004/0002616 A1 | * 1/2004 | Preto et al. | ..................... 562/2 |

FOREIGN PATENT DOCUMENTS

| | | | | |
|---|---|---|---|---|
| EP | 0147207 | * 7/1985 | | |
| EP | 0 596 493 | 5/1994 | | |
| EP | 0953283 | * 11/1999 | | |
| JP | 2003081711 A | * 3/2003 | .......... A01N/37/02 |
| WO | WO 98/37762 | 9/1998 | | |
| WO | WO 00/29038 | 5/2000 | | |
| WO | WO 01/82694 | 11/2001 | | |

OTHER PUBLICATIONS

S.S. Block: "Disinfection, Sterilization, and Preservation." Fourth edition, Chapter 9: Peroxygen Compounds, pp. 167–181, 1991. Lea & Febiger, Philadelphia, US, XP002256830.

* cited by examiner

Primary Examiner—Matthew A. Thexton
(74) Attorney, Agent, or Firm—Oblon, Spivak, McClelland, Maier & Neustadt, P.C.

(57) ABSTRACT

A sterilizing composition for a food-packing material which comprises the following components (1) and (2):

(1) an aqueous solution containing peracetic acid, hydrogen peroxide and acetic acid, and (2) a peracetic acid sterilizing power-improving agent comprising one or two or more compounds selected from the group consisting of esters obtained from a $C_2$–$C_8$ aliphatic acid and a $C_2$–$C_8$ aliphatic alcohol, $C_2$–$C_8$ aliphatic alcohols and aliphatic alcohols having a benzene ring.

7 Claims, No Drawings

STERILIZING COMPOSITION AND METHOD FOR STERILIZING USING THE SAME

BACKGROUND OF THE INVENTION

1. Field of the Invention

The present invention relates to a sterilizing composition usable for sterilizing a food-packing material such as a polyethylene terephthalate packing material, and also relates to a sterilizing method using the same.

2. Discussion of Background

Examples of an industrial sterilizing method for a polyethylene terephthalate packing material, particularly a polyethylene terephthalate bottle (PET bottle), include a hot packing method and an aseptic packing method.

The hot packing method comprises a system of sterilizing a packed content at an ultra-high temperature (UHT) and then packing the content into a container at 85 to 87° C., and examples of pollutant bacteria include bacteria spores derived from a production line or a container. On the other hand, the aseptic packing method comprises a system of sterilizing a packed content at UHT and then packing the sterilized content into a chemically sterilized container under an aseptic environment (NASA Standard Class 100), and examples of pollutant bacteria include chemically tolerable mold or bacteria spores.

It is known that examples of an agent for sterilizing a packing material in the aseptic packing method include peroxide type compounds such as hydrogen peroxide, ozone or peracetic acid, and chlorine type compounds such as chlorine or sodium hypochlorite. Among them, peracetic acid is widely used since it has an immediate effect and a strong sterilizing power even at a low concentration, and also it has a wide antibacterial spectrum and achieves an excellent effect for sterilizing bacteria spores, molds or yeasts.

Molds, bacteria spores and the like are not produced in a container such as an aluminum can, a steel can or a glass bottle, wherein a packed content can be maintained in an anaerobic state, but in case of an air-permeable PET bottle, the anaerobic state can not be maintained during storing for a long term, and there is a fear that anaerobic bacteria spores such as bacillus or molds such as chaetomium are produced. In order to prevent the production of these bacteria in a food-processing step, it is necessary to raise a temperature or a concentration of a sterilizing agent or to prolong a treating time.

However, if a concentration of a sterilizing agent is raised, there is a problem that a treating agent such as peracetic acid, hydrogen peroxide or acetic acid is likely attached or remained on a food-packing material even after sterilizing and washing steps. Also, if a temperature is raised, there are problems that a PET bottle or the like tends to be deformed by heat and consequently that a heat resistant packing material must be used.

In order to solve these problems, JP-A-10-323385 proposes a two step-sterilizing method comprising a combination of a sterilizing step of using a peroxide such as peracetic acid and a sterilizing step of using decyldimethyl ammonium chloride, but this method simply aims at achieving a synergistic effect of two kinds of sterilizing agents.

The present inventors have noted that the above problems can be solved and peracetic acid can be used substantially at a low concentration by improving a sterilizing power of a peracetic acid aqueous solution.

An object of the present invention is to discover a material which can improve a sterilizing power of a peracetic acid aqueous solution and to provide a sterilizing composition (for a food-packing material) which can stably sterilize with peracetic acid at a substantially low concentration without changing an apparatus, an equipment or sterilizing conditions, and also to provide a sterilizing method using the same.

The present inventors have intensively studied in order to achieve the above object, and discovered that a sterilizing power of a peracetic acid aqueous solution can be enhanced (achieving a synergistic effect) by adding a specific compound to an aqueous solution containing peracetic acid, hydrogen peroxide and acetic acid, and the present invention has been accomplished on the basis of this discovery.

SUMMARY OF THE INVENTION

The present invention provides a sterilizing composition for a food-packing material such as polyethylene terephthalate, characterized by containing the following components (1) and (2):

(1) an aqueous solution containing peracetic acid, hydrogen peroxide and acetic acid, and (2) a peracetic acid sterilizing power-improving agent comprising one or two or more compounds selected from the group consisting of esters obtained from a $C_2$–$C_8$ aliphatic acid and a $C_2$–$C_8$ aliphatic alcohol, $C_2$–$C_8$ aliphatic alcohols and aliphatic alcohols having a benzene ring.

Further, the present invention provides a method for sterilizing a food-packing material, which comprises contacting a food-packing material with a sterilizing composition containing the following components (1) and (2) and then washing the food-packing material with a sterilized water:

(1) an aqueous solution containing peracetic acid, hydrogen peroxide and acetic acid, and (2) a peracetic acid sterilizing power-improving agent comprising one or two or more compounds selected from the group consisting of esters obtained from a $C_2$–$C_8$ aliphatic acid and a $C_2$–$C_8$ aliphatic alcohol, $C_2$–$C_8$ aliphatic alcohols and aliphatic alcohols having a benzene ring.

Still further, the present invention provides a sterilizing composition characterized by containing the following components (1) and (2'):

(1) an aqueous solution containing peracetic acid, hydrogen peroxide and acetic acid, and (2') a peracetic acid sterilizing power-improving agent comprising one or two or more compounds selected from the group consisting of esters obtained from a $C_3$–$C_8$ aliphatic acid and a $C_3$–$C_8$ saturated aliphatic alcohol, $C_2$–$C_4$ aliphatic alcohols, $C_7$–$C_8$ aliphatic alcohols and aliphatic alcohols having a benzene ring represented by the following formula,

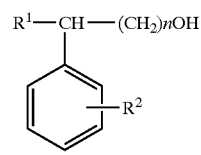

wherein n is an integer of from 0 or 2 to 4, $R^1$ is a hydrogen atom or a $C_1$–$C_4$ alkyl group, and $R^2$ is a hydrogen atom, a $C_1$–$C_4$ alkyl group or a halogen atom.

DETAILED DESCRIPTION OF THE PREFERRED EMBODIMENTS

Hereinafter, the present invention is described in more details.

A sterilizing composition of the present invention for a food-packing material can be prepared by adding a peracetic acid sterilizing power-improving agent to an aqueous solution containing peracetic acid, hydrogen peroxide and acetic acid previously prepared. That is, it is preferable to prepare the sterilizing composition of the present invention for a food-packing material by diluting the previously prepared aqueous solution containing peracetic acid, hydrogen peroxide and acetic acid so as to provide a predetermined peracetic acid concentration and then adding a predetermined amount of the peracetic acid sterilizing power-improving agent thereto. If the sterilizing composition is prepared in this manner, it provides a concentration which can be used as it is for a sterilizing step.

Among the peracetic acid sterilizing power-improving agents used in the present invention, examples of esters obtained from a $C_2$–$C_8$ aliphatic acid and a $C_2$–$C_8$ aliphatic alcohol include ethyl acetate, propyl acetate, amyl acetate, isoamyl acetate, ethyl propionate, butyl propionate, isoamyl propionate, ethyl butyrate, isoamyl butyrate, ethyl valerate, ethyl hexanoate, amyl hexanoate, isoamyl hexanoate, ethyl enanthoate, ethyl caprylate, amyl caprylate and isoamyl caprylate.

Examples of a $C_2$–$C_8$ aliphatic alcohol include ethanol, propanol, isopropyl alcohol, butanol, n-amyl alcohol, n-hexanol and n-heptanol.

Also, examples of an aliphatic alcohol having a benzene ring include preferably an alcohol represented by the formula,

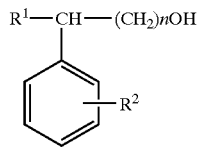

wherein n is an integer of from 0 to 5, $R^1$ is a hydrogen atom or a $C_1$–$C_4$ alkyl group, and $R^2$ is a hydrogen atom, a $C_1$–$C_4$ alkyl group or a halogen atom.

More particular examples include benzyl alcohol, methylbenzyl alcohol, ethylbenzyl alcohol, isopropylbenzyl alcohol, tert-butylbenzyl alcohol, chlorobenzyl alcohol, 2-phenyl ethanol, 3-phenyl-1-propyl alcohol, 2-phenyl-1-propyl alcohol, 1-phenyl-1-propyl alcohol, 4-phenyl-1-butanol and phenyl pentanol.

Among them, ethanol, propanol, benzyl alcohol and phenyl butanol are particularly preferable in respect of their performances of improving a sterilizing power of peracetic acid and their solubility.

Among these peracetic acid sterilizing power-improving agents, one or two or more compounds selected from the group consisting of esters obtained from a $C_3$–$C_8$ aliphatic acid and a $C_2$–$C_8$ saturated aliphatic alcohol, $C_2$–$C_4$ aliphatic alcohols, $C_7$–$C_8$ aliphatic alcohols and aliphatic alcohols having a benzene ring represented by the following formula, are suitably usable for sterilization of materials other than a food-packing material:

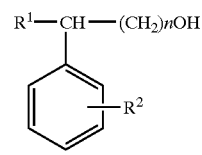

wherein n is an integer of from 0 or 2 to 4, $R^1$ is a hydrogen atom or a $C_1$–$C_4$ alkyl group, and $R^2$ is a hydrogen atom, a $C_1$–$C_4$ alkyl group or a halogen atom.

Also, a sterilizing composition having a sterilizing power improved (for a food-packing material) can be obtained by incorporating an anionic surfactant into a sterilizing composition containing the above components (1) and (2) or (2') (for a food-packing material), and therefore, an anionic surfactant may be optionally incorporated therein.

Examples of an anionic surfactant includes a sulfonate type anionic surfactant such as an alkylsulfonate, an alkylbenzenesulfonate, a dialkylsulfosuccinic acid ester salt or an α-olefin sulfonate, a sulfate type anionic surfactant such as a higher alcohol sulfuric acid salt (an alkyl sulfate) or a polyoxyethylene alkyl ether sulfate, and a carboxylate type anionic surfactant such as a polyoxyethylene alkyl ether carboxylate. These surfactants sometimes generate foams, and if the generation of foams is not preferable, their use may be optionally controlled.

With regard to a concentration of each component of a sterilizing composition used for a sterilizing step (for a food-packing material), peracetic acid is used at a concentration of from 1,000 to 4,000 ppm, hydrogen peroxide is used at a concentration of from 1,500 to 30,000 ppm and acetic acid is used at a concentration of from 2,000 to 30,000 ppm, and a concentration of a peracetic acid sterilizing power-improving agent is varied depending on a kind of a peracetic acid sterilizing power-improving agent used due to a difference in its solubility and is determined in view of its solubility, but is preferably from 1,000 ppm to 10%.

With regard to the concentration of a peracetic acid sterilizing power-improving agent, an easily soluble material such as ethanol, propanol, isopropanol, benzyl alcohol or methylbenzyl alcohol is used preferably at a concentration of from 1 to 10%, more preferably from 2 to 8%, since a sterilizing power of the sterilizing composition is more highly enhanced if its addition amount is increased. Also, a material having a relatively low solubility or a hardly soluble material such as amyl acetate, isoamyl acetate, isoamyl caprylate, ethyl butyrate, pentyl acetate or heptanol, is used preferably at a concentration of from 1,500 ppm to 1%, more preferably from 2,000 to 9,000 ppm, and it may be used in a suspension state depending on a case required.

When using an anionic surfactant, its concentration is preferably from 10 to 5,000 ppm, more preferably from 100 to 2,000 ppm.

A sterilizing effect of the above sterilizing composition (for a food-packing material) is more enhanced as a temperature of the composition is raised, but a satisfactory performance for sterilizing mold, heat-resistant bacteria spores and the like deposited or generated on a food-packing material can be fully achieved at a temperature of from 40 to 65° C.

The sterilizing composition of the present invention (for a food-packing material) is suitable for sterilizing a food-packing material, particularly a polyethylene terephthalate packing material such as a polyethylene terephthalate bottle, and the sterilization of a PET bottle is carried out for example as illustrated below.

(1) A sterilizing composition (chemical solution) of the present invention for a food-packing material is sprayed on the outer surface of a PET bottle to wash the outside of the bottle.

(2) Thereafter, the sterilizing composition (chemical solution) for a food-packing material at a temperature of from 40 to 65° C. is sprayed or fully filled into the inside of the PET bottle to sterilize the inside of the bottle.

(3) After discharging the sterilizing composition (chemical solution) for a food-packing material, the PET bottle is washed with a sterilized water in order to remove the sterilizing composition (chemical solution) for a food-packing material attached to the inside and the outside of the PET bottle.

EXAMPLES

Hereinafter, the present invention is further concretely illustrated by the following Examples.

Example 1
Preparation of Test Sample Solution
(a) Preparation of Peracetic Acid Aqueous Solution 95 g of tap water was added to 5 g of an equilibrated peracetic acid solution containing 4 wt % of peracetic acid, 16 wt % of hydrogen peroxide and 15 wt % of acetic acid, and the resultant mixture was stirred to prepare a uniform aqueous solution. A peracetic acid concentration of the aqueous solution thus prepared was 2,000 ppm.

(b) Preparation of Sterilizing Power Test Sample Solution

Each of sterilizing power test sample solutions was prepared by adding a predetermined amount of each of peracetic acid sterilizing power-improving agents shown in the following Table 1 to the peracetic acid aqueous solution prepared in the above paragraph (a) and stirring the mixture.

Test Method of Sterilizing Power 100 ml of the above prepared test sample solution was placed in an Erlenmeyer flask, and was maintained at 40° C. 1 ml of a chaetomium spore solution having an inoculated bacteria number of 4×10⁶ CFU/ml was inoculated therein, and 1 ml of a sample was taken from the Erlenmeyer flask respectively at 10 seconds, 20 seconds, 30 seconds, 60 seconds and 120 seconds after the inoculation. Each of the samples thus taken was immediately placed in 9 ml of an inactivating agent containing a reductive material of sodium sulfite as a base to terminate sterilizing activities of peracetic acid. Thereafter, a number of live bacteria remaining in each sample optionally diluted was measured in accordance with plate mix-diluting cuture method using a potato dextrose agar medium, and a D value (time (unit: minute) taken to reduce a bacteria number to 1/10) was determined as a standard of sterilizing power. A sterilizing power is stronger as the D value is smaller.

The results are shown in the following Table 1.

TABLE 1

| Experiment No. | Peracetic acid concentration (ppm) | Sterilizing power-improving agent Kind of sterilizing power-improving agent | Addition amount (ppm) | $D_{40}$ |
|---|---|---|---|---|
| 1 | 2000 | — | 4000 | 2.19 |
| 2 | 0 | Amyl acetate | 4000 | 210 |
| 3 | 0 | Amyl caprylate | 4000 | 59 |
| 4 | 0 | Isopropyl alcohol | 4000 | 150 |
| 5 | 0 | n-amyl alcohol | 4000 | 331 |
| 6 | 0 | n-hexanol | 4000 | 102 |
| 7 | 0 | n-heptanol | 4000 | 98 |
| 8 | 0 | 2-phenyl ethanol | 4000 | 238 |
| 9 | 2000 | Amyl acetate | 4000 | 1.80 |
| 10 | 2000 | Amyl caprylate | 4000 | 1.71 |
| 11 | 2000 | Isopropyl alcohol | 4000 | 1.96 |
| 12 | 2000 | n-hexanol | 4000 | 1.03 |
| 13 | 2000 | n-heptanol | 4000 | 1.17 |
| 14 | 2000 | 2-phenyl ethanol | 4000 | 1.90 |
| 15 | 2000 | Ethyl hexanoate | 9000 | 1.79 |
| 16 | 2000 | Amyl acetate | 9000 | 1.22 |
| 17 | 2000 | Ethyl acetate | 9000 | 1.88 |
| 18 | 2000 | Isoamyl acetate | 9000 | 1.10 |
| 19 | 2000 | Amyl alcohol | 9000 | 1.41 |
| 20 | 2000 | n-hexanol | 9000 | 0.81 |
| 21 | 2000 | n-heptanol | 9000 | 1.17 |
| 22 | 2000 | 2-phenyl ethanol | 9000 | 0.78 |
| 23 | 2000 | Isoamyl caprylate | 9000 | 1.61 |
| 24 | 2000 | Benzyl alcohol | 9000 | 1.42 |
| 25 | 2000 | Ethyl valerate | 9000 | 1.81 |
| 26 | 2000 | Ethyl enanthoate | 9000 | 1.90 |
| 27 | 2000 | Isoamyl propionate | 9000 | 1.93 |

Example 2

A sample solution (peracetic acid concentration: 2,000 ppm, n-heptanol concentration: 4,000 ppm) having the same composition as experiment No. 13 of Example 1 was prepared. The sample solution heated at 40° C. was sprayed on the outer surface of a PET bottle carried by a conveyer to sterilize the outside of the bottle. The bottle having the outside sterilized was transferred by a conveyer into a sterilizing room called as a sterilizing tunnel, where the above sample solution heated at 40° C. was fully filled into the bottle to sterilize the inside of the bottle for 2 minutes. The bottle was then turned over to discharge the sample solution, and a sterilized water was sprayed onto the outside and the inside of the bottle to wash and remove the sample solution attached to the outside and the inside of the bottle. Thereafter, green tea was filled into the bottle, and the bottle was sealed with a sterilized cap and was allowed to stand at 30° C. for 14 days, but no mold was generated.

Example 3
Preparation of Test Sample Solution
(a) Preparation of Peracetic Acid Aqueous Solution 98.5 g of tap water was added to 1.5 g of an equilibrated peracetic acid solution containing 10 wt % of peracetic acid, 17 wt % of hydrogen peroxide and 20 wt % of acetic acid, and the resultant mixture was stirred to prepare a uniform aqueous solution. A peracetic acid concentration of the aqueous solution thus prepared was 1,500 ppm.

(b) Preparation of Sterilizing Power Test Sample Solution

Each of sterilizing power test sample solutions was prepared by adding a predetermined amount of a peracetic acid sterilizing power-improving agent or a combination of a peracetic acid sterilizing power-improving agent and an anionic surfactant to the above-prepared peracetic acid aqueous solution (a) as shown in the following Table 2 and stirring the mixture.

Test Method of Sterilizing Power 100 ml of each of the above prepared test sample solutions was placed in an Erlenmeyer flask, and was maintained at 40° C. 1 ml of a bacteria spore solution (Bacillus polymyxa peracetic acid-tolerable bacteria) having a bacteria number of $2.7 \times 10^6$ CFU/ml was inoculated therein, and 1 ml of a sample was taken respectively at 10 seconds, 20 seconds, 30 seconds, 60 seconds and 120 seconds from the Erlenmeyer flask and immediately placed in 9 ml of an inactivating agent containing sodium sulfite as a base. Thereafter, the sample was optionally diluted, and live bacteria was measured in accordance with plate mix-diluting cuture method using a standard above medium to determine a D value.

The results are shown in the following Table 2.

TABLE 2

| Experiment No. | Peracetic acid concentration (ppm) | Sterilizing power-improving agent | | Anionic surfactant | | $D_{40}$ |
|---|---|---|---|---|---|---|
| | | Kind of sterilizing power-improving agent | Addition amount (ppm) | Kind (*1) | Addition amount (ppm) | |
| 1 | 1500 | — | | | | 3.38 |
| 2 | 0 | Ethanol | 5.0 | — | | 7.41 |
| 3 | 0 | Benzyl alcohol | 2.3 | — | | 4.41 |
| 4 | 0 | 4-phenyl-1-butanol | 0.2 | | | 10.7 |
| 5 | 1500 | — | | SHSS | 1000 | 3.10 |
| 6 | 1500 | Ethanol | 2.5 | | | 1.27 |
| 7 | 1500 | Ethanol | 5.0 | | | 0.55 |
| 8 | 1500 | Propanol | 5.0 | | | 0.31 |
| 9 | 1500 | Isopropanol | 5.0 | | | 1.05 |
| 10 | 1500 | Heptanol | 0.1 | | | 1.31 |
| 11 | 1500 | Heptanol | 0.1 | SHSS | 1000 | 0.15 |
| 12 | 1500 | Heptanol | 0.1 | SDS | 500 | 0.30 |
| 13 | 1500 | Heptanol | 0.15 | SDS | 1000 | 0.08 |
| 14 | 1500 | Heptanol | 0.15 | SDBS | 1000 | 0.08 |
| 15 | 1500 | Benzyl alcohol | 2.3 | | | 0.3 |
| 16 | 1500 | 4-methylbenzyl alcohol | 1.0 | | | 0.74 |
| 17 | 1500 | 4-chlorobenzyl alcohol | 1.0 | | | 0.57 |
| 18 | 1500 | 4-tert-butylbenzyl alcohol | 0.3 | | | 1.42 |
| 19 | 1500 | 3-phenyl-1-propyl alcohol | 0.5 | | | 1.41 |
| 20 | 1500 | 4-phenyl-1-butanol | 0.2 | | | 1.68 |
| 21 | 1500 | 4-phenyl-1-butanol | 0.2 | SDBS | 1000 | 0.28 |
| 22 | 1500 | 4-phenyl-1-butanol | 0.2 | SHSS | 1000 | 0.15 |
| 23 | 1500 | 4-phenyl-1-butanol | 0.4 | | | 0.64 |
| 24 | 1500 | 4-phenyl-1-butanol | 0.4 | SHSS | 1000 | 0.08 |

(Note) (*1)
SDS: sodium 1-dodecanesulfonate
SDBS: sodium dodecylbenzenesulfonate
SHSS: sodium di-2-hexyl sulfosuccinate As evident from the above results, a sterilizing power of a peracetic acid aqueous solution in a sterilizing composition of the present invention (for a food-packing material) is highly enhanced, and bacteria which has been conventionally hardly sterilized can be sterilized by peracetic acid substantially at a low concentration and at a low temperature. Thus, the sterilizing composition of the present invention is suitably usable for sterilizing a food-packing material such as a polyethylene terephthalate bottle.

The entire disclosure of Japanese Patent Application No. 2002-181323 filed on Jun. 21, 2002 including specification, claims and summary are incorporated herein by reference in its entirety.

What is claimed is:

1. A sterilizing composition for a food-packaging material, which consists of the following components (1) and (2):
   (1) an aqueous solution containing peracetic acid, hydrogen peroxide and acetic acid, and
   (2) a peracetic acid sterilizing power-improving agent which is benzyl alcohol in an amount ranging from 2 to 8 wt %, based on the total weight of the aqueous composition.

2. A sterilizing composition for a food-packaging material, which consists of the following components (1) and (2):
   (1) an aqueous solution containing from 0.1 to 0.4 wt % peracetic acid, from 0.15 to 3 wt % hydrogen peroxide and from 0.2 to 3 wt % acetic acid, each based on the total weight of the aqueous composition, and
   (2) a peracetic acid sterilizing power-improving agent which is benzyl alcohol in an amount ranging from 2 to 8 wt %, based on the total weight of the aqueous composition.

3. The sterilizing composition according to claim 2, wherein the packaging material is made of polyethylene terephthalate.

4. A sterilizing composition for a food-packaging material, which consists of the following components (1) and (2):
   (1) an aqueous solution containing peracetic acid, hydrogen peroxide and acetic acid, and
   (2) a peracetic acid sterilizing power-improving agent which is benzyl alcohol in an amount ranging from 2 to 8 wt %, based on the total weight of the aqueous composition; and
   (3) an anionic surfactant.

5. A sterilizing composition for a food-packaging material, which consists of the following components (1) and (2):
   (1) an aqueous solution containing from 0.1 to 0.4 wt % peracetic acid, from 0.15 to 3 wt % hydrogen peroxide and from 0.2 to 3 wt % acetic acid, each based on the total weight of the aqueous composition;

(2) a peracetic acid sterilizing power-improving agent which is benzyl alcohol in an amount ranging from 2 to 8 wt %, based on the total weight of the aqueous composition; and (3) an anionic surfactant.

6. A method for sterilizing a food-packaging material, which comprises:

contacting the food-packaging material with a sterilizing composition consisting of the following components (1) and (2):

(1) an aqueous solution containing peracetic acid, hydrogen peroxide and acetic acid, and (2) a peracetic acid sterilizing power-improving agent which is benzyl alcohol in an amount ranging from 2 to 8 wt %, based on the total weight of the aqueous composition; and then washing the food-packaging material with sterilized water.

7. A sterilizing composition, which consists of the following components (1) and (2):

(1) an aqueous solution containing from 0.1 to 0.4 wt % peracetic acid, from 0.15 to 3 wt % hydrogen peroxide and from 0.2 to 3 wt % acetic acid, each based on the total weight of the aqueous composition, and (2) a peracetic acid sterilizing power-improving agent which is benzyl alcohol in an amount ranging from 2 to 8 wt %, based on the total weight of the aqueous composition.

* * * * *